United States Patent [19]

Yano et al.

[11] Patent Number: 5,304,656

[45] Date of Patent: Apr. 19, 1994

[54] PROCESS FOR PREPARING ALKYLENE SULFIDES

[75] Inventors: Hitoshi Yano; Yoshinari Yamaguchi; Kimio Ariyoshi; Yuuji Shimasaki, all of Suita; Ryuichi Ishikawa, Sakai; Michio Ueshima, Takarazuka, all of Japan

[73] Assignee: Nippon Shokubai Co., Ltd., Osaka, Japan

[21] Appl. No.: 980,009

[22] Filed: Nov. 23, 1992

[30] Foreign Application Priority Data

Nov. 29, 1991 [JP] Japan ................... 3-316657
Nov. 29, 1991 [JP] Japan ................... 3-316658

[51] Int. Cl.$^5$ .......................................... C07D 331/02
[52] U.S. Cl. ............................................. 549/1
[58] Field of Search .................................. 549/1, 90

[56] References Cited

U.S. PATENT DOCUMENTS 3,622,597 11/1971 Fletcher ........................ 260/327
3,687,976 8/1972 Wright ........................... 260/327

FOREIGN PATENT DOCUMENTS 6512117 3/1966 Netherlands .
7001172 6/1970 Netherlands .
1092610 11/1967 United Kingdom ............. 549/1
1135800 12/1968 United Kingdom .

OTHER PUBLICATIONS

"Cyclodehydration of 2-Mercaptoalkanols as a Route to Episulphides", J. Chem. Soc. (C), 1969, pp. 1252 to 1256.

Primary Examiner—Richard L. Raymond
Assistant Examiner—Mary Cebulak
Attorney, Agent, or Firm—Jordan and Hamburg

[57] ABSTRACT

In a process for preparing alkylene sulfides through the intramolecular dehydration reaction of mercaptoalkanols in a gaseous phase, catalysts are used, which are represented by the formula: $M_aX_bY_cO_d$, where M represents at least one element selected from the group of alkali metals, alkaline earth metals and thallium; X represents at least one element selected from the group of Al, B, Si and P; Y represents at least one element selected from the group consisting of lanthanides, IIIA group, IVA group, VA group, IIIB group, IVB group, VB group and VIB group, excluding an element contained in M or X; O represents oxygen; and a and b are numerical values not equal to 0; b=0.2–100 and c=0–50 when a=1; and d is a numerical value determined according to a, b and c.

9 Claims, No Drawings

PROCESS FOR PREPARING ALKYLENE SULFIDES

BACKGROUND OF THE INVENTION

The present invention relates to a process for preparing alkylene sulfides by an intramolecular dehydration reaction of mercaptoalkanols in a gaseous phase under the presence of catalysts.

Alkylene sulfides, which have superior reactivity, are useful compounds that are extensively used as manufacturing materials for pharmaceuticals, pesticides, and various industrial chemicals as well as being used as a reactant for sulfur-containing polymers.

Concerning processes for manufacturing alkylene sulfides, U.S. Pat. No. 3,687,976 as well as U.K. Pat. No. 1135800 disclose a process wherein ethylene oxide reacts with carbonyl sulfide or carbon disulfide under the presence of catalysts. However, this process has problems with the toxicity of carbonyl sulfide and carbon disulfide as well as with the low yield of alkylene sulfide as a target product.

Further, U.S. Pat. No. 3,622,597 and J. Chem. Soc. (C), p1252-1256, 1969, disclose a process for preparing alkylene sulfides, wherein a mercaptoethanol is subjected to an intramolecular dehydration reaction in a liquid phase under the presence of a catalyst of sulfuric acid series. However, this process suffers from drawbacks wherein the yield of alkylene sulfide as a target product is low because of a large amount of polymerization by-products; and it is expensive to separate the polymerization by-products from the catalyst after the reaction since the reaction is a homogeneous reaction in the liquid phase. Therefore, it is impossible to put this process into practical industrial use.

Moreover, Netherlands Pat. No. 7001172 discloses a process for obtaining alkylene sulfides through the intramolecular dehydration reaction of mercaptoalkanols in a gaseous phase, which is carried out by using solid catalysts such as titanium oxide, zirconium oxide or niobium oxide. It is described that in accordance with this method, alkylene sulfides can be obtained in a high yield from mercaptoalkanols. However, no description is found in the specification concerning catalyst life, which is a very important factor to stably manufacture the target products, alkylene sulfides. According to examinations carried out by the inventors of the present application, in the case of using the catalysts such as titanium oxide, zirconium oxide or niobium oxide, since the acid property of the catalysts is too strong, so-called coking develops during the reaction such that deactivation of the catalysts proceeds quickly. Moreover, in addition to the quick deactivation of the catalysts, $MgTiO_3$ and $SrTiO_3$ that are, disclosed in the above Laid-Open Patent Publication, they have extremely low activity in comparison with such a catalyst as titanium oxide. Therefore, it has been shown that this method using these catalysts fails to provide a satisfactory method from the industrial point of view.

SUMMARY OF THE INVENTION

It is an object of the present invention to provide a process by which alkylene sulfides are stably and efficiently obtained from mercaptoalkanols in a high yield for a long period.

In order to achieve the above objective, the inventors of the present application have found that, in a process for preparing alkylene sulfides from mercaptoalkanols, by making mercaptoalkanols subject to an intramolecular dehydration reaction in a gaseous phase under the presence of novel catalysts, alkylene sulfides can be stably obtained in a high yield for a long period. The catalysts employed are composite oxides having, as essential ingredients, both of at least one element selected from the group consisting of alkali metals, alkaline earth metals and thallium and at least one element selected from the group consisting of aluminum, boron, silicon and phosphorous.

More specifically, the present invention provides a process for preparing alkylene sulfides of the formula:

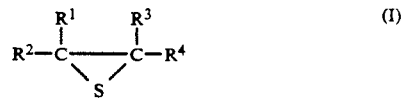

wherein $R^1$, $R^2$, $R^3$ and $R^4$ are respectively selected from the group consisting of a hydrogen atom, an alkyl group with 1–4 carbon atoms, a phenyl group, and a benzyl group, which is obtained through the intramolecular dehydration reaction of mercaptoalkanols of the formula:

wherein $R^1$, $R^2$, $R^3$ and $R^4$ are as defined above, in a gaseous phase, the process being characterized by the use of catalysts of the formula:

wherein M represents at least one element selected from the group consisting of alkali metals, alkaline earth metals and thallium; X represents at least one element selected from the group consisting of aluminum, boron, silicon and phosphorous; Y represents at least one element selected from the group consisting of lanthanides, IIIA group, IVA group, VA group, IIIB group, IVB group, VB group and VIB group (excluding an element contained in M or X); and O represents oxygen, while subscripts a, b, c and d respectively represent composition ratios of the elements; a and b are numerical values not equal to 0; b=0.2–100 and c=0–50 when a=1; and d is a numerical value determined according to a, b and c.

In accordance with the present invention, alkylene sulfides are stably manufactured from mercaptoalkanols with high selectivity for a long period. Moreover, since no secondary reactants are required for the process, few by-products are produced. Thus, the present invention has succeeded in providing a very simple and economical process.

DETAILED DESCRIPTION OF THE PREFERRED EMBODIMENTS

Suitable mercaptoalkanols to be used as a reactant in the present invention include 2-mercaptoethanol, 1-methyl-2-mercaptoethanol, 1-ethyl-2-mercaptoethanol, 1,2-dimethyl-2-mercaptoethanol and 1-phenyl-2-mercaptoethanol. In accordance with the process of the present invention, the corresponding alkylene sulfides can be obtained depending on the mercaptoalkanols employed.

The catalysts used in the present invention ar composite oxides represented by the aforementioned formula (III). These composite oxides exhibit catalytic performances in a gaseous phase reaction such that alkylene sulfides are stably obtained from mercaptoalkanols in a high yield and with a high selectivity for a long period. In particular, in the case of manufacturing ethylene sulfide which exhibits a remarkably high reactivity among alkylene sulfides, if catalysts of the formula (III) with X containing at least one element selected from the group consisting of boron and phosphorous are used, more preferable results can be obtained.

As to the reason why the catalysts of the present invention exhibit superior performances in the intramolecular dehydration reaction from mercaptoalkanols to alkylene sulfides, it has not been clarified in detail. However, active sites on the surface of the catalysts not only accelerate the intramolecular dehydration reaction of mercaptoalkanols, but also have extremely inactive characteristics toward produced alkylene sulfides; therefore, the consecutive reactions are inhibited. As a result, having less occurrence of coking, the target products can be obtained in a high yield.

Moreover, in these catalysts, special emphasis is placed on the acid and base property on the surface of the catalysts, and generally a remarkable effect has been found especially in their life of the catalysts which have acid sites ranging from $+3.3$ to $+7.0$ and base sites ranging from $+7.0$ to $+9.3$ in the acid-base strength $H_0$ that is measured by Hammett's indicator method.

Additionally, the acid-base strength $H_0$ is measured through the following method:

0.1 g of a catalyst, which has been dried at 250° C. for two hours, was immersed into 1 ml of anhydrous benzene in a test tube, and ten of these samples were prepared. Then, two or three drops of benzene solutions containing the following indicators were added to the respective samples, and stirred, and then left to rest at room temperature for 24 hours. The benzene solutions used as Hammett's indicators were: dicinnamal acetone ($H_0 = -3.0$), 4-(phenylazo)diphenylamine ($H_0 = +1.5$), p-dimethyl-aminoazobenzene ($H_0 = +3.3$), phenylazonaphthylamine ($H_0 = 4.0$), methyl red ($H_0 = +4.8$), neutral red ($H_0 = +6.8$), bromthymol blue ($H_0 = +7.2$), m-nitrophenol ($H_0 = +8.3$), phenolphthalein ($H_0 = +9.3$), and 2,4,6-trinitroaniline ($H_0 = +12.2$). The ($H_0$) value of the sample at acid site was determined by the smallest ($H_0$) value among the Hammett's indicators which had been subjected to color changes and which had the ($H_0$) value of less than $+7.0$. Similarly, the ($H_0$) value of the sample at base site was determined by the greatest ($H_0$) value among the Hammett's indicators which had been subjected to color changes and which had the ($H_0$) value of more than $+7.0$.

As for materials for the catalysts, various materials such as metal elements, oxides, hydroxides, halides, nitrates, sulfates, phosphates, and carbonates may be employed.

The preparation method of the catalysts is not necessarily limited to a specific one; various preparation methods that are commonly used may be adopted. For example, those methods include: a method wherein various catalyst materials, which are dissolved or suspended in water and heated and condensed while stirring, are formed after being dried and further calcined to form a catalyst; a method wherein various catalyst materials, which are dissolved or suspended in water and changed into a hydroxide by adding ammonia water thereto, are filtrated and rinsed in water, and then dried to form a catalyst; and a method wherein oxides or hydroxides of various elements are ground and mixed, and after being dried and formed, are calcined to form a catalyst. As for the calcining temperatures of the catalysts, although they depend on the materials to be used and on the calcining time, temperatures of 300° C.-1000° C. are suitable in the air or in an atmosphere of inert gas (such as nitrogen, argon, or helium). Further, the catalysts of the present invention may be used in such a manner wherein they are carried on inert supports, for example, such as diatomaceous earth, kaolinite, silicon carbide, or silicon nitride.

In carrying out the gaseous-phase reaction of the present invention, any type of reactor may be employed among the fixed bed flowing type, the fluidized bed type and the moving bed type.

Moreover, mercaptoalkanol a reactant may be supplied into the reactor, either diluted or not diluted. In the case of supplying it in a diluted state, an inactive gas such as nitrogen, helium or argon may be used as a diluent gas. Here, the concentration of the reactant is preferably set to not less than 5% by volume since an extremely low concentration of the reactant causes a decrease in productivity. Generally, the reaction is conducted under reduced or normal pressure; but, the reaction may be conducted under a pressurized atmosphere.

The space velocity of the reactant gas, although it varies depending on the composition of the reactant gas, the reaction temperature and the reaction pressure, is set in the range of 10-10000 h$^{-1}$ during the reaction. The reaction temperature is in the range of 180° C.-350° C., preferably 200° C.-320° C. If the reaction temperature is below 180° C., the catalyst activity will be too low to get a sufficient yield. On the contrary, if the reaction temperature is above 350° C., secondary reactions will occur preferentially so that the selectivity of the target alkylene sulfides becomes low.

The following description will discuss the present invention in detail by reference to experimental examples and comparative examples. Here, the conversion of mercaptoalkanols, the selectivity of alkylene sulfides and the yield are determined according to the following definitions.

The conversion of mercaptoalkanols (%) = (the number of moles of mercaptoalkanols consumed through the reaction/the number of moles of mercaptoalkanols supplied) × 100.

The selectivity of alkylene sulfides (%) = (the number of moles of alkylene sulfides produced/the number of moles of mercaptoalkanols consumed) × 100.

The yield of alkylene sulfides (%) = (the number of moles of alkylene sulfides produced/the number of moles of mercaptoalkanols supplied) × 100.

EXAMPLE 1

To a solution prepared by dissolution of 1.2 grams of cesium nitrate and 3.9 grams of boric acid in 250 ml of water was added 34 grams of silica gel. The mixture was heated and condensed, and then dried at 130° C. for 11 hours. The resulting solid matter was calcined at 600° C. in the air for 3 hours; thus, a catalyst with a composition represented by $Cs_1B_{10}Si_{90}$ in the atomic ratio excluding oxygen was obtained. The catalyst having the composition of $Cs_1B_{10}Si_{90}$ thus obtained was crushed into powder of 4-9 mesh and loaded into a reaction tube. Then, the reaction tube was immersed into a melt salt bath at 270° C., and a reactant gas was introduced into the reaction tube at a space velocity of 3000 $^{-1}$. The reactant gas had a composition ratio of 2-mercaptoethanol:nitrogen = 10:90 in the volume ratio. The reaction conditions are shown in Tables 1 and 2.

The products of the reaction were analyzed by gas chromatography, and the results shown in Table 3 were obtained.

In the following examples 2 through 18, each catalyst was prepared by each method as shown below. Here, reactions and analyses were performed in the same manner as Example 1 except that: the kind of mercaptoalkanol, as a reactant; the concentration of a reactant gas; the space velocity; the reaction temperature; and the reaction pressure were all changed as indicated in Tables 1 and 2. Consequently, the results shown in Tables 3 were obtained.

EXAMPLE 2

A solution was prepared by dissolution of 4.2 grams of sodium nitrate and 367.8 grams of aluminum nitrate in 2000 ml of water. Then, a 28% solution of ammonia water was added to the solution with stirring carried out for two hours while maintaining the pH of the solution in the range from 8 to 10. After cooling-off, filtration, and water rinse processes, white powder was obtained. The powder was dried for 14 hours at 120° C., and then calcined at 700° C. in the air for three hours; consequently, a catalyst with a composition represented by $Na_1Al_{20}$ in the atomic ratio excluding oxygen was obtained.

EXAMPLE 3

To a solution prepared by dissolution of 7.6 grams of rubidium nitrate and 0.5 grams of sodium nitrate in 170 ml of water was consecutively added 6.5 grams of an 85% solution of phosphoric acid and 34 grams of silica. The mixture was heated and condensed, and then dried at 140° C. for 12 hours.

The resulting solid matter was calcined at 600° C. in the air for three hours; consequently, a catalyst with a composition represented by $Rb_{0.9}Na_{0.1}P_1Si_{10}$ in the atomic ratio excluding oxygen was obtained.

EXAMPLES 4 AND 5

4.2 grams of sodium hydroxide (purity 95%), 8.1 grams of a 85% solution of orthophosphoric acid, and 30 grams of silicon carbide (whisker) as a support were suspended in 200 ml of water, and the mixture was heated and condensed at 80° C. with sufficient stirring. The resulting solid matter, after having been dried at 120° C. in the air for 12 hours, was calcined at 600° C. in the air for two hours; consequently, a catalyst with a composition represented by $Na_1P_{0.7}$ in the atomic ratio excluding support element and oxygen was obtained.

EXAMPLE 6

To a solution prepared by dissolution of 10.1 grams of potassium nitrate and 11.9 grams of diammonium hydrogen phosphate in 200 ml of water was added 30 grams of silica gel. The mixture was heated and condensed, and then dried at 120° C. for 12 hours. The resulting solid matter was calcined at 600° C. in the air for three hours; consequently, a catalyst with a composition represented by $K_1P_{0.9}Si_5$ in the atomic ratio excluding oxygen was obtained.

EXAMPLE 7

To a solution prepared by dissolution of 8.2 grams of boric acid and 2.1 grams of thallium nitrate in 200 ml of hot water having a temperature of 80° C. were added 5.9 grams of barium hydroxide octahydrate and 70.8 grams of niobium pentoxide in powder. The mixture was heated and condensed, and then sufficiently dried at 120° C. The resulting solid matter was calcined at 600° C. in the air for two hours; consequently, a catalyst with a composition represented by $Tl_{0.3}Ba_{0.7}B_5Nb_{20}$ in the atomic ratio excluding oxygen was obtained.

EXAMPLE 8

A solution prepared by dissolution of 6.2 grams of potassium hydroxide (purity 90%) and 30.9 grams of boric acid in 300 ml of hot water having a temperature of 80° C. was added to 56.5 grams of yttrium oxide in powder. The mixture was heated and condensed, and then sufficiently dried at 120° C. in the air. The resulting solid matter was calcined at 650° C. in the air for six hours; consequently, a catalyst with a composition represented by $K_1B_5Y_5$ in the atomic ratio excluding oxygen was obtained.

EXAMPLE 9

A mixture was prepared by mixing 2.9 grams of cerium(IV) oxide and 40 grams of titanium oxide, both in powder. To the mixture was added a mixed solution prepared by dissolution of 16.9 grams of potassium nitrate and 22.0 grams of diammonium hydrogen phosphate in 300 ml of water. The mixture was heated and condensed, and then sufficiently dried at 120° C. The resulting solid matter was calcined at 600° C. in the air for two hours; consequently, a catalyst with a composition represented by $K_1P_1Ce_{0.1}Ti_3$ in the atomic ratio excluding oxygen was obtained.

EXAMPLE 10

A solution was prepared by dissolution of 86.6 grams of lanthanum nitrate hexahydrate and 3.9 grams of cesium nitrate in 500 ml of water. To the solution was added 26.5 grams of diammonium hydrogen phosphate, and the mixture was heated and condensed with sufficient stirring, and then sufficiently dried at 120° C. The resulting solid matter was calcined at 750° C. in the air for three hours; consequently, a catalyst with a composition represented by $Cs_1P_{10}La_{10}$ in the atomic ratio excluding oxygen was obtained.

EXAMPLE 11

To a solution prepared by dissolution of 5.3 grams of strontium nitrate and 2.1 grams of sodium nitrate in 300 ml of water was added 61.6 grams of zirconium oxide in powder with sufficient stirring. Then, 4.0 grams of diammonium hydrogen phosphate was added to the mixture, and it was heated and condensed, and then sufficiently dried at 130° C. The resulting powder was calcined at 650° C. in the air for three hours; consequently, a catalyst whose composition was represented by $Na_{0.5}Sr_{0.5}P_{0.6}Zr_{10}$ in the atomic ratio excluding oxygen was obtained.

EXAMPLE 12

A mixture prepared by mixing and grinding 16.5 grams of sodium tungstic acid dihydrate and 30 grams of silica gel in a mortar was further kneaded with 100 ml of water. The resulting slurry was sufficiently dried at 130° C., and then calcined at 600° C. in the air for three hours; consequently, a catalyst with a composition represented by $Na_1Si_5W_{0.5}$ in the atomic ratio excluding oxygen was obtained.

EXAMPLE 13

To a solution prepared by dissolution of 88.0 grams of diammonium hydrogen phosphate in 800 ml of water was added 74.1 grams of calcium hydroxide, and the mixture was evaporated and dried hard, thereby resulting in a solid matter. The solid matter was calcined at 600° C. in the air for three hours; consequently, a catalyst with a composition represented by $Ca_1P_{0.66}$ in the atomic ratio excluding oxygen was obtained.

EXAMPLE 14

To a solution prepared by dissolution of 321.7 grams of lithium nitrate and 205.3 grams of diammonium hydrogen phosphate in 300 ml of water was added 28% ammonia water to adjust the pH of the solution to 8-10 with stirring carried out for two hours. Then, the mixture was cooled off, filtered and rinsed in water, thereby resulting in white powder. The white powder was calcined at 600° C. in the air for three hours; consequently, a catalyst with a composition represented by $Li_1P_{0.33}$ in the atomic ratio excluding oxygen was obtained.

EXAMPLE 15

To a solution prepared by dissolution of 43.4 grams of strontium nitrate in 200 ml of water was added 50 grams of aluminum phosphate. The solution was heated and condensed, and then dried at 130° C. for ten hours. The resulting solid matter was calcined at 600° C. in the air for three hours; consequently, a catalyst with a composition represented by $Sr_1Al_2P_2$ in the atomic ratio excluding oxygen was obtained.

EXAMPLE 16

A mixture was prepared by mixing and grinding in a mortar 3.5 grams of gallium oxide in powder and 50 grams of kaolin powder as a support. Then, to the mixture was added a solution prepared by dissolution of 9 grams of sodium dihydrogen phosphate in 300 ml of water, and the mixture was heated and condensed. The resulting solid matter was sufficiently dried at 120° C., and then calcined at 500° C. in the air for six hours; consequently, a catalyst with a composition represented by $Na_1P_1Ga_{0.5}$ in the atomic ratio excluding support atoms and oxygen was obtained.

EXAMPLE 17

A mixture was prepared by sufficiently mixing and grinding in a mortar 5.4 grams of boric acid, 3.9 grams of barium hydroxide octahydrate, 40 grams of titanium oxide in powder, and 13.1 grams of germanium oxide in powder. After adding 200 ml of 50° C. warm water thereto, the mixture was heated and condensed. The resulting solid matter was sufficiently dried at 120° C., and then calcined at 750° C. in the air for three hours; consequently, a catalyst with a composition represented by $Ba_1B_7Ge_{10}Ti_{40}$ in the atomic ratio excluding oxygen was obtained.

EXAMPLE 18

A solution was prepared by dissolution of 10.5 grams of dipotassium hydrogen phosphate in 200 ml of water. After adding thereto 1.7 grams of antimony(III) oxide in powder and 30.6 grams of alumina powder, the mixture was heated and condensed. The resulting solid matter was sufficiently dried at 120° C. and then calcined at 800° C. in the air for four hours; consequently, a catalyst with a composition represented by $K_1P_{0.5}Al_5Sb_{0.2}$ in the atomic ratio excluding oxygen was obtained.

TABLE 1

| Example | Catalyst Composition $M_a$ | $X_b$ | $Y_c$ | Acid-Base Strength $H_0$ Acid Site | Base Site |
|---|---|---|---|---|---|
| 1 | $Cs_1$ | $B_{10}Si_{90}$ | — | +3.3 | +7.2 |
| 2 | $Na_1$ | $Al_{20}$ | — | +4.0 | +7.2 |
| 3 | $Na_{0.1}Rb_{0.9}$ | $P_1Si_{10}$ | — | +4.0 | +8.3 |
| 4 | $Na_1$ | $P_{0.7}$ | — | +6.8 | +8.3 |
| 5 | $Na_1$ | $P_{0.7}$ | — | +6.8 | +8.3 |
| 6 | $K_1$ | $P_{0.9}Si_5$ | — | +4.8 | +8.3 |
| 7 | $Tl_{0.3}Ba_{0.7}$ | $B_5$ | $Nb_{20}$ | +3.3 | +7.2 |
| 8 | $K_1$ | $B_5$ | $Y_5$ | +4.0 | +7.2 |
| 9 | $K_1$ | $P_1$ | $Ce_{0.1}Ti_3$ | +4.0 | +7.2 |
| 10 | $Cs_1$ | $P_{10}$ | $La_{10}$ | +4.8 | +8.3 |
| 11 | $Na_{0.5}Sr_{0.5}$ | $P_{0.6}$ | $Zr_{10}$ | +4.0 | +8.3 |
| 12 | $Na_1$ | $Si_5$ | $W_{0.5}$ | +4.8 | +8.3 |
| 13 | $Ca_1$ | $P_{0.66}$ | — | +6.8 | +9.3 |
| 14 | $Li_1$ | $P_{0.33}$ | — | +4.8 | +9.3 |
| 15 | $Sr_1$ | $Al_2P_2$ | — | +6.8 | +8.3 |
| 16 | $Na_1$ | $P_1$ | $Ga_{0.5}$ | +4.0 | +8.3 |
| 17 | $Ba_1$ | $B_7$ | $Ge_{10}Ti_{40}$ | +4.8 | +8.3 |
| 18 | $K_1$ | $P_{0.5}Al_5$ | $Sb_{0.2}$ | +6.8 | +9.3 |

TABLE 2

| Example | Reactant | Space Velocity ($h^{-1}$) | Temp. (°C.) | Reactant Ratio (Vol. %) | Pressure (mmHg) |
|---|---|---|---|---|---|
| 1 | 2-mercaptoethanol | 3000 | 270 | 10 | 760 |
| 2 | 1,2-dimethyl-2-mercaptoethanol | 2000 | 250 | 20 | 760 |
| 3 | 2-mercaptoethanol | 4000 | 270 | 10 | 760 |
| 4 | 2-mercaptoethanol | 3000 | 270 | 10 | 760 |
| 5 | 2-mercaptoethanol | 400 | 300 | 100 | 80 |
| 6 | 2-mercaptoethanol | 2000 | 250 | 10 | 760 |
| 7 | 1-methyl-2-mercaptoethanol | 2000 | 270 | 10 | 760 |
| 8 | 2-mercaptoethanol | 4000 | 300 | 20 | 760 |
| 9 | 2-mercaptoethanol | 2500 | 300 | 20 | 760 |
| 10 | 2-mercaptoethanol | 2000 | 230 | 10 | 760 |
| 11 | 1-methyl-2-mercaptoethanol | 200 | 200 | 100 | 150 |
| 12 | 1-methyl-2-mercaptoethanol | 1500 | 300 | 10 | 760 |
| 13 | 2-mercaptoethanol | 300 | 300 | 100 | 80 |
| 14 | 1-phenyl-2-mercaptoethanol | 7000 | 300 | 5 | 1000 |
| 15 | 1,2-dimethyl-2-mercaptoethanol | 200 | 270 | 100 | 80 |
| 16 | 2-mercaptoethanol | 2000 | 300 | 10 | 760 |
| 17 | 2-mercaptoethanol | 2500 | 270 | 10 | 760 |
| 18 | 2-mercaptoethanol | 2000 | 300 | 10 | 760 |

TABLE 3

| Example | Product | Elapsed Time (hr) | Conversion (%) | Selectivity (%) | Yield (%) |
|---|---|---|---|---|---|
| 1 | ethylene sulfide | 1 | 87.4 | 95.1 | 83.1 |
|  |  | 200 | 84.0 | 95.1 | 79.9 |
| 2 | 2,3-dimethyl ethylene sulfide | 1 | 87.2 | 93.1 | 81.2 |
|  |  | 50 | 84.9 | 95.6 | 81.1 |
| 3 | ethylene sulfide | 1 | 86.3 | 95.4 | 82.3 |
|  |  | 100 | 86.2 | 96.1 | 82.8 |
| 4 | ethylene sulfide | 2 | 95.1 | 93.2 | 88.6 |
|  |  | 200 | 93.7 | 93.4 | 87.5 |
| 5 | ethylene sulfide | 2 | 93.6 | 97.1 | 90.9 |
|  |  | 200 | 90.8 | 97.5 | 88.5 |
| 6 | ethylene sulfide | 2 | 97.1 | 98.3 | 95.4 |
|  |  | 200 | 96.5 | 98.7 | 95.2 |
| 7 | 2-methyl ethylene sulfide | 1 | 84.4 | 92.2 | 77.8 |
|  |  | 100 | 83.0 | 91.9 | 76.3 |
| 8 | ethylene sulfide | 2 | 93.6 | 94.7 | 88.6 |

TABLE 3-continued

| Example | Product | Elapsed Time (hr) | Conversion (%) | Selectivity (%) | Yield (%) |
|---|---|---|---|---|---|
|  |  | 100 | 91.5 | 95.3 | 87.2 |
| 9 | ethylene sulfide | 2 | 93.8 | 92.6 | 86.9 |
|  |  | 200 | 93.5 | 92.8 | 86.8 |
| 10 | ethylene sulfide | 2 | 87.2 | 93.3 | 81.4 |
|  |  | 100 | 82.9 | 92.5 | 76.7 |
| 11 | 2-methyl | 2 | 95.9 | 96.2 | 92.3 |
|  | ethylene sulfide | 100 | 95.5 | 95.8 | 91.5 |
| 12 | 2-methyl | 2 | 88.8 | 91.6 | 81.3 |
|  | ethylene sulfide | 50 | 85.9 | 92.3 | 79.3 |
| 13 | ethylene sulfide | 1 | 90.6 | 94.6 | 85.7 |
|  |  | 100 | 90.0 | 94.3 | 84.9 |
| 14 | 2-phenyl | 1 | 84.8 | 97.7 | 82.8 |
|  | ethylene sulfide | 100 | 83.2 | 97.9 | 81.5 |
| 15 | 2,3-dimethyl | 1 | 89.4 | 91.6 | 81.9 |
|  | ethylene sulfide | 100 | 87.1 | 93.3 | 81.3 |
| 16 | ethylene sulfide | 1 | 92.3 | 91.1 | 84.1 |
|  |  | 100 | 89.9 | 93.7 | 84.2 |
| 17 | ethylene sulfide | 1 | 87.6 | 94.1 | 82.4 |
|  |  | 100 | 85.9 | 93.7 | 80.5 |
| 18 | ethylene sulfide | 1 | 96.3 | 92.4 | 89.0 |
|  |  | 100 | 93.0 | 91.9 | 85.5 |

COMPARATIVE EXAMPLES 1-4

Concerning each of the catalysts prepared in accordance with the following comparative examples 1-4, reactions and analyses were performed in the same manner as Example 1 except that: the kind of mercaptoalkanol, as a reactant; the concentration of a reactant gas; the space velocity; the reaction temperature; and the reaction pressure were changed as indicated in Table 4. Consequently, the results shown in Table 5 were obtained.

COMPARATIVE EXAMPLE 1

A mixture prepared by addition of 50 grams of commercial niobium pentoxide to 100 ml of water was heated and condensed, and then sufficiently dried at 150° C. The resulting solid matter was calcined at 600° C. in the air for three hours; consequently, a catalyst with a composition represented by $Nb_1$ in the atomic ratio excluding oxygen was obtained.

COMPARATIVE EXAMPLE 2

A mixture prepared by addition of 50 grams of titanium oxide (rutile type) in powder to 100 ml of water was heated and condensed, and then dried at 150° C. The resulting solid matter was calcined at 600° C. in the air for three hours; consequently, a catalyst with a composition represented by $Ti_1$ in the atomic ratio excluding oxygen was obtained.

COMPARATIVE EXAMPLE 3

A mixture prepared by addition of 50 grams of commercial strontium titanate to 100 ml of water was heated and condensed, and then dried at 150° C. The resulting solid matter was calcined at 500° C. in the air for three hours; consequently, a catalyst with a composition represented by $Sr_1Ti_1$ in the atomic ratio excluding oxygen was obtained.

COMPARATIVE EXAMPLE 4

To a solution prepared by dissolution of 8.8 grams of diammonium hydrogen phosphate in 130 ml of water was added 40 grams of silica gel. The mixture was heated and condensed, and then dried at 140° C. for ten hours. The resulting solid matter was calcined at 600° C. in the air for three hours; consequently, a catalyst with a composition represented by $P_1Si_{10}$ in the atomic ratio excluding oxygen was obtained.

TABLE 4

| * | Catalyst Composition | | | Acid-Base Stren. ($H_0$) | | Reactant | Space Velocity ($h^{-1}$) | Temp (°C.) | Reactant ratio (V %) | Pressure (mmHg) |
|---|---|---|---|---|---|---|---|---|---|---|
|  | $M_a$ | $X_b$ | $Y_c$ | Acid Site | Base Site |  |  |  |  |  |
| 1 | — | — | $Nb_1$ | +1.5 | — | 2-mercapto ethanol | 2000 | 275 | 20 | 760 |
| 2 | — | — | $Ti_1$ | +3.3 | — | 2-mercapto ethanol | 2000 | 270 | 10 | 760 |
| 3 | $Sr_1$ | — | $Ti_1$ | +6.8 | +7.2 | 2-mercapto ethanol | 2000 | 270 | 10 | 760 |
| 4 | — | $P_1Si_{10}$ | — | −3.0 | — | 2-mercapto ethanol | 2000 | 250 | 20 | 760 |

*Comparative Example

TABLE 5

| Comparative Example | Product | Elapsed Time (hr) | Conversion (%) | Selectivity (%) | Yield (%) |
|---|---|---|---|---|---|
| 1 | ethylene sulfide | 1 | 95.1 | 70.0 | 66.6 |
|  |  | 30 | 48.5 | 67.8 | 32.9 |
| 2 | ethylene sulfide | 1 | 86.7 | 71.1 | 61.6 |
|  |  | 30 | 36.4 | 73.9 | 26.8 |
| 3 | ethylene sulfide | 1 | 16.2 | 76.3 | 12.4 |
|  |  | 30 | 10.8 | 73.9 | 8.0 |
| 4 | ethylene sulfide | 1 | 93.4 | 3.2 | 3.0 |

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A process for preparing alkylene sulfides of the formula

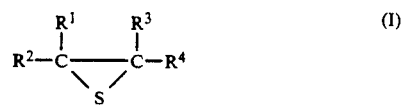

wherein $R^1$, $R^2$, $R^3$ and $R^4$ are respectively selected from the group consisting of a hydrogen atom, an alkyl group with 1-4 carbon atoms, a phenyl group, and a benzyl group, comprising:

carrying out the intramolecular dehydration reaction of mercaptoalkanols of the formula

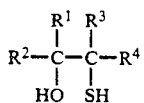 (II)

wherein $R^1$, $R^2$, $R^3$ and $R^4$ are as defined above, in a gaseous phase at a reaction temperature in the range from 180° C. to 350° C., in the presence of catalysts of the formula $$M_a X_b Y_c O_d \quad \text{(III)}$$

wherein M represents at least one element selected from the group consisting of alkali metals, alkaline earth metals and thallium; X represents at least one element selected from the group consisting of aluminum, boron, silicon and phosphorous; Y represents at least one element selected from the group consisting of lanthanides, IIIA group, IVA group, VA group, IIIB group, IVB group, VB group and VIB group, excluding an element contained in M or X; O represents oxygen; and subscripts a, b, c and d respectively represent composition ratios of the elements; a and b are numerical values not equal to 0; b=0.2–100 and c=0–50 when a=1; and d is a numerical value which is consistent with the valency of a, b and c so as to give a neutrally charged catalyst moiety.

2. The process as defined in claim 1, wherein in formula (III), c is a value not equal to 0; and Y represents at least one element selected from the group consisting of lanthanum, cerium, yttrium, titanium, zirconium and niobium.

3. The process as defined in claim 1, wherein in formula (III), c is equal to 0.

4. The process as defined in claim 1, wherein in formula (III), X includes at least one element selected from the group consisting of boron and phosphorus.

5. The process as defined in claim 1, wherein the catalyst has acid sites ranging from +3.3 to +7.0 and base sites ranging from +7.0 to +9.3 in the acid-base strength $H_0$ that is measured by the Hammett' indicator method.

6. The process for preparing alkylene sulfides as defined in claim 1, wherein alkylene sulfide and mercaptoalkanol are ethylene sulfide and 2-mercaptoethanol respectively.

7. The process for preparing alkylene sulfides as defined in claim 6, wherein in formula (III), X includes at least one element selected from the group consisting of boron and phosphorus.

8. The process for preparing alkylene sulfides as defined in claim 1, wherein the reaction is carried out at a temperature in the range from 200° C. to 320° C.

9. The process for preparing alkylene sulfides as defined in claim 1, wherein the concentration of the mercaptoalkanol is not less than 5% by volume.

* * * * *